US008639526B2

(12) United States Patent
Gibbs

(10) Patent No.: US 8,639,526 B2
(45) Date of Patent: Jan. 28, 2014

(54) SYSTEM AND METHOD FOR DIAGNOSIS AND EARLY TREATMENT ADOPTION FOR ASYMPTOMATIC DISEASE

(76) Inventor: Chris Gibbs, Gainesville, FL (US)

( * ) Notice: Subject to any disclaimer, the term of this patent is extended or adjusted under 35 U.S.C. 154(b) by 171 days.

(21) Appl. No.: 12/713,831

(22) Filed: Feb. 26, 2010

(65) Prior Publication Data

US 2010/0330537 A1  Dec. 30, 2010

Related U.S. Application Data

(60) Provisional application No. 61/208,636, filed on Feb. 26, 2009.

(51) Int. Cl.
*G06Q 10/00* (2012.01)
*G06Q 50/00* (2012.01)

(52) U.S. Cl.
USPC ............................................................ 705/2

(58) Field of Classification Search
USPC .................................................... 705/2, 3
See application file for complete search history.

(56) References Cited

U.S. PATENT DOCUMENTS

| 7,329,116 | B2 | 2/2008 | Dohman et al. | |
| 7,860,725 | B2 * | 12/2010 | Gopinathan et al. | 705/2 |
| 2006/0154210 | A1 * | 7/2006 | Martin et al. | 433/215 |
| 2006/0212316 | A1 * | 9/2006 | Jackson et al. | 705/3 |
| 2006/0270935 | A1 * | 11/2006 | Ariff et al. | 600/437 |
| 2007/0219419 | A1 * | 9/2007 | KenKnight et al. | 600/300 |

* cited by examiner

*Primary Examiner* — John Pauls
*Assistant Examiner* — Trang Nguyen
(74) *Attorney, Agent, or Firm* — Saliwanchik, Lloyd & Eisenschenk

(57) ABSTRACT

Systems and methods are provided for diagnosis of and early treatment adoption for asymptomatic diseases. In one embodiment, an examination system is provided including an input device for entering patient data, a computer including a medium for storing entered data, and a feedback module for providing feedback to an examined patient based on the data entered. A method of using the examination system is also provided in which feedback is provided directly to the patient concurrently with the measurement or other acquisition of a significant data point. Feedback is also provided at the conclusion of the examination in the form of a report, treatment plan, or customized educational materials. In a further embodiment, the patient is an active participant in the examination, recording data points themselves via the input device.

6 Claims, 11 Drawing Sheets

SYSTEM AND METHOD FOR DIAGNOSIS AND EARLY TREATMENT ADOPTION FOR ASYMPTOMATIC DISEASE

CROSS-REFERENCE TO A RELATED APPLICATION

This application claims the benefit of U.S. provisional application Ser. No. 61/208,636, filed Feb. 26, 2009, which is incorporated herein by reference in its entirety.

BACKGROUND OF INVENTION

In developed countries, over half of all adults have some form of periodontal disease. See, e.g., Sheila Riggs, *Public Policy & Oral Health: A Whole New Game*, Scientific American, Special Supplement, *Oral and Whole Body Health*, 2006, at 39 ("57 percent of adults have moderate periodontitis; 7 to 15 percent have an advanced form of the disease."). Recent studies have linked periodontal disease to other significant health problems including heart disease, stroke, diabetes, and premature birth. E.g., Philip E. Ross, *Invaders of the Body's Defenses*, Scientific American, Special Supplement, *Oral and Whole Body Health*, 2006, at 6.

Thankfully, a variety of relatively inexpensive treatment options for periodontal disease are emerging. But many of these treatment options are only indicated when the disease is in its early stages. Later, treatment options become increasingly invasive and expensive, often requiring oral surgery and/or treatment of the associated problems caused by the periodontal disease. Therefore, early detection and treatment of periodontal disease is important to ensure the best outcomes and decrease health care costs.

Unfortunately, current methods of early diagnosis of periodontal disease are underutilized, cumbersome, and/or prone to errors. For example, voice activated periodontal charting systems are available that allow a registered dental hygienist or other trained examiner to document periodontal disease during examination. But these systems must be trained to the voice of the particular examiner and can introduce errors into the patient's chart. In a periodontal examination producing 500-1000 data points, an error rate of just 4% produces 20-40 errors per examination. These errors must either be corrected in front of the patient or left uncorrected.

Other available systems provide automated voice confirmation to detect and correct errors, but these systems provide no feedback or education to the patient. For example, Logue (U.S. Pat. No. 7,329,116) discloses a foot-operated data entry device including an automated voice system, but the voice system merely announces data values to be entered into a computer-based chart. The system merely repeats the data entered via the input device without any additional feedback or educational messages for the patient. Such feedback and education is critical because, unlike other dental problems, early periodontal disease is often not accompanied by pain or visible symptoms that inform the patient of the seriousness of the problem. Hygienists and other dental professionals have a difficult time convincing patients to treat a problem they can neither see nor feel.

The normative roles of different participants in the examination and diagnosis process can also be a barrier to early treatment adoption. Often times the persons who have the most interaction with a patient, such as nurses, assistants, and hygienists, develop an emotional attachment to the patient. This type of caring open relationship is important to patient care as well as to the success of a practice. But, if the nurse, hygienist, or other representative of the practice becomes reluctant to deliver "bad news" to the patient because of this attachment, the patient's care may suffer and the practice may be exposed to liability for failure to properly inform the patient of their condition and associated risks.

The changing normative role of doctors, dentists, and other licensed professionals can also become a barrier to treatment when a patient's expectations are not met. Younger generations of patients may be less prone to respect a professional's authority without question. These patients may seek a more in-depth understanding of their condition and treatment options. Such patients increasingly seek out other sources of information on their own via high-technology sources, such as the Internet, or require more information from their doctors or other dental and health care professionals. Professionals who have been practicing a long time may not be accustomed to being questioned in depth by this new generation of patients. They may consider such activities as "selling" a patient on a treatment. They may feel that sales interaction with a patient is undignified and inappropriate for a professional. But if professionals do not respond well to a patient's inquires, the patient may take their questions elsewhere, or worse, rely on a misunderstanding of information they themselves find on the Internet. Again, patient care may suffer and a practice may be exposed to liability as a result.

Accordingly, there is need for a less cumbersome method for periodontal examination that also educates patients and encourages early treatment adoption. There is also need for an authoritative, unbiased, third-party "voice" in a practice that can deliver in-depth, customized condition and treatment information to patients in a manner that is efficient, engaging, effective, consistent, and documentable, without risking caring patient relationships.

Periodontal disease is highlighted here as an illustrative example of an asymptomatic disease that would benefit form early diagnosis and treatment adoption. The subject invention can also be applied to other medical diseases.

BRIEF SUMMARY

Embodiments of the present invention include improved systems and methods for diagnosis and early treatment adoption for asymptomatic disease. Embodiments of the invention may be best suited for situations where patients initially resist necessary treatment and therefore effective patient education is indicated. Embodiments of the invention also serve to document patient examination, education, and refusal of treatment to provide a clear record in the event of later litigation or other adverse claims.

In one aspect of an embodiment of the subject invention, an examination system is provided including an input device for entering patient data and a computer including a medium for storing entered data and a feedback module for providing feedback in various forms to an examined patient based on the data entered. The data can be entered by an examiner and/or by the patient themselves. The feedback can be immediate, or it can be delayed until after the examination is complete.

In another embodiment of the subject invention, a method is provided for diagnosis of disease and early adoption of treatment for the disease. According to this method, an examination system is used during examination of the patient. The system provides feedback directly to the patient. In a preferred embodiment of the invention, the feedback is provided during the course of the examination concurrently with the measurement or other acquisition of a significant data point. In another embodiment, feedback is provided at the conclusion of the examination in the form of a report, treatment plan, or customized educational materials. Feedback is presented in such a manner as to engage as many of the patient's five senses as possible. In a further embodiment of the invention, the patient is an active participant in the examination, recording data points themselves via, for example, a handheld input device.

In yet another aspect of an embodiment of the subject invention, one or more computer-readable media are provided, which embody a method for diagnosis of disease and early adoption of treatment for the disease, such as the methods described above.

It should be noted that this Brief Summary is provided to generally introduce the reader to one or more select concepts described below in the Detailed Disclosure in a simplified form. This Summary is not intended to identify key and/or required features of the claimed subject matter. The invention is defined by the claims below.

BRIEF DESCRIPTION OF DRAWINGS

The file of this patent contains at least one drawing executed in color. Copies of this patent with color drawings(s) will be provided by the Patent and Trademark Office upon request and payment of the necessary fee.

DETAILED DISCLOSURE

Figure 1:
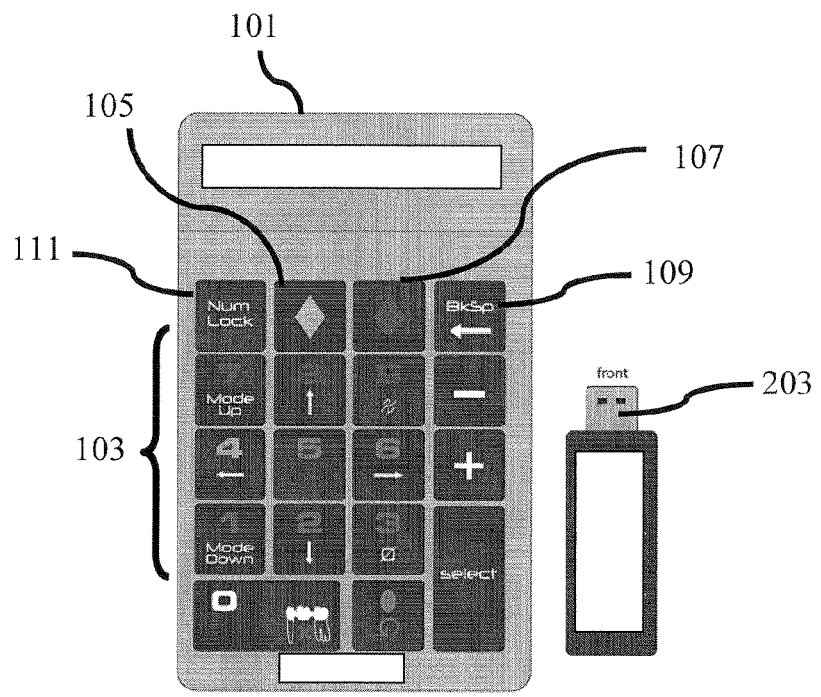
FIG. 1 shows an input device in accordance with an embodiment of the subject invention.

Embodiments of the present invention include improved systems and methods for diagnosis and early treatment adoption for asymptomatic disease. Diagnosis and treatment adoption for periodontal disease is described here in detail to illustrate the invention, but the invention is applicable to the diagnosis and treatment of any number of injuries and diseases.

The subject matter of the present invention is described with specificity to meet statutory requirements. But this description is not intended to limit the scope of this patent. Rather, the inventors have contemplated that the claimed subject matter might also be embodied in other ways, to include different steps or combinations of steps similar to those described in this document, in conjunction with other present or future technologies. Moreover, although the term "step" may be used herein to connote different elements of methods employed, the term should not be interpreted as implying any particular order among or between various steps herein disclosed unless and except when the order of individual steps is explicitly described. Further, the present invention is described in detail below with reference to the attached drawing figures, which are incorporated in their entirety by reference herein.

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In one embodiment, the present invention takes the form of a computer-program product that includes computer-useable instructions embodied on one or more computer-readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow, a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

In an embodiment of the subject invention, a system for entering medical or dental patient data is provided including an input device, a host computer, and a feedback module. The input device can be any number of standard or customized input devices as further discussed below. The input device may be portable to be brought into an examination, operating, or procedure room or can be fixed to an examination table, chair, or other handy surface.

As further discussed below, the input device may be adapted for use by a hygienist, nurse, dentist, doctor, or other trained professional, or habituated user. In another embodiment of the invention, the input device is simplified for use by a novice user or the patient themselves. In yet another embodiment of the invention, as further discussed below, the device is able to switch between two input modes: one adapted to a trained user; and the other adapted to a novice user or patient.

As is well known in the art of plug-and-play devices, the input device can communicate with the host computer via a Universal Serial Bus (USB) port, among other known methods, and instantly load drivers to mimic a standard keypad, mouse, or other data entry device for entry of data or cursor navigation in a software application, such as practice management or charting software, running on the host computer. The input device can also be installed and drivers loaded via other methods known in the art.

In an embodiment of the subject invention, the input device can be one of many in use in an office or other site installation. Even if each such input device communicates with a separate host computer in close proximity using wireless communication technology, well known methods can be employed to ensure that the input devices do not cross-talk or communicate information to the wrong host. A single input device can also be quickly moved from one computer to another.

As further illustrated below, various keys, buttons, switches, touchpads, trackballs, joysticks, or other well known input controls can be provided on the input device and used to enter data or observations related to a patient into a software application running on the host computer, such as charting or practice management software. Further, the input device can be programmed to allow a set of key strokes or control manipulations to combine to enter a single or multiple data points. In a particular embodiment, the input device contains a memory and apparatus for programming and reprogramming the device to store new sets of keys and controls to work with different applications, computers, or computer programs.

FIG. 1 shows an input device 101 in accordance with an embodiment of the subject invention. As discussed above, the input device 101 can be used to enter patient data into a computer-based patient chart or other software application. Various quantitative observations can be entered via the device including but not limited to measurements of the body, test results, respirations per minute, blood pressure, among other metrics. Qualitative observations can also be entered including but not limited to the presence of blood, puss, or inflammation at an examination site, heart murmurs, disorientation, among other observations. The examples provided here are merely illustrative. Other observations can be entered by way of the input device 101.

The observations or data points may be entered into the input device 101 in a predetermined sequence, so that the position in which a particular data point is entered corresponds to a data field in a chart, or other patient record, where the particular data point belongs. In an embodiment, the examiner pre-sets the sequence of the examination before the examination begins. Entries can be abbreviated or coded so that they can be entered using fewer keystrokes. For example, numeric data may be entered via the numeric keys 103. In another embodiment of the invention, alphabetical keys are provided on an input device, such as a standard or minimized keyboard.

Custom keys may also be programmed to enter a particular number, phrase, or other data. In the example provided here, custom keys 105 and 107 are used to indicate the presence of puss and blood respectively. Other custom data entry keys can be provided on the input device 101. Such keys can display icons or pictures to be easily identified by a novice user. Keys can also contain shapes that can be identified by feel or can be arranged in a recognizable layout to facilitate data entry by a novice user such as the patient. Keys may also be color coded to convey information to such a user. For example, green may be used for keys used to enter healthy parameters, red may be used on keys used to enter dangerous or unhealthy parameters, and yellow may be used to enter middle-ground or warning parameters. Also spring pressure of keys or height of keys can be used to represent different importance levels or meanings related to treatment or disease levels.

Cursor navigation keys may also be provided. Here, the backspace key 109 deletes a single entered data point. In other embodiments, the backspace key 109 returns to the beginning of the previous field and a forward key is provided so that navigation between data fields can be accomplished without deletion. Other keystroke navigation buttons are known in the art, such as Home, End, Page Up, and Page Down keys, and may be used with the subject invention.

The input device 109 can be incorporated into a host computer which stores, accesses, or displays the data points and other patient information, such as a computer running charting or practice management software. In a further embodiment, the input device 109 is incorporated into a separate, mobile electronic device, such as a handheld device, which communicates with a host computer using any wired or wireless communication technology known in the art.

Figure 2:
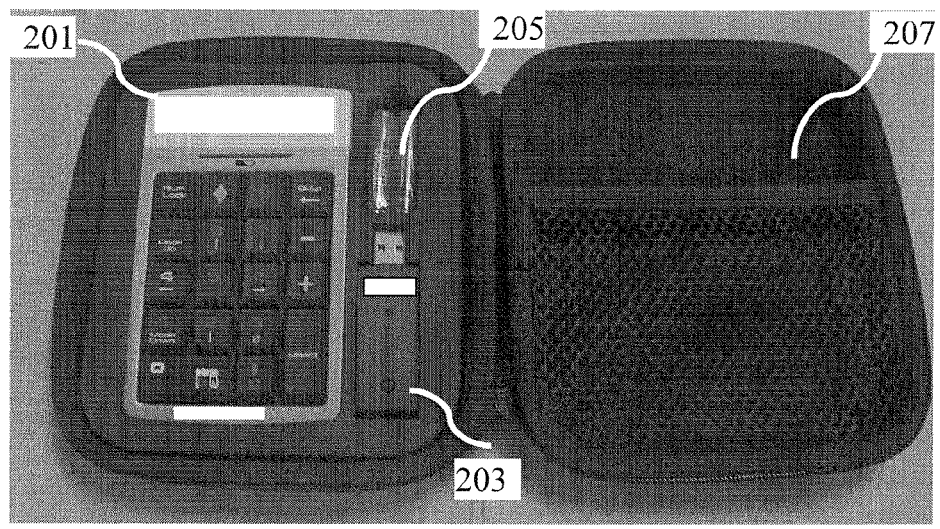
FIG. 2 shows the input device of FIG. 1 along with accessories in accordance with an embodiment of the subject invention.

FIG. 2 shows the input device of FIG. 1 201 along with a carrying case 207 and other accessories used with the input device 201. Batteries 205 are shown which can be used to power the input device 201. Other power supply methods are well known in the art, such as rechargeable batteries and ac adapters, and can be used to supply power to the input device 201. A wireless receiver 203 is also shown (also shown in FIG. 1) which can be attached to a host computer to facilitate wireless communication between the input device 201 and the host computer. As discussed above, various wireless communication methods are well known in the art and can be used with the subject invention.

Figure 3:
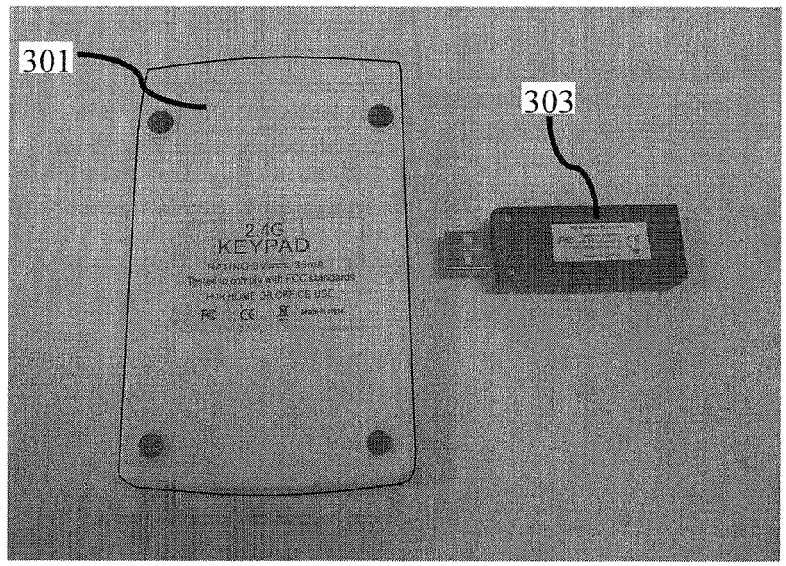
FIG. 3 shows a back view of the input device of FIG. 1 along with a wireless receiver in accordance with an embodiment of the subject invention.
Figure 4:
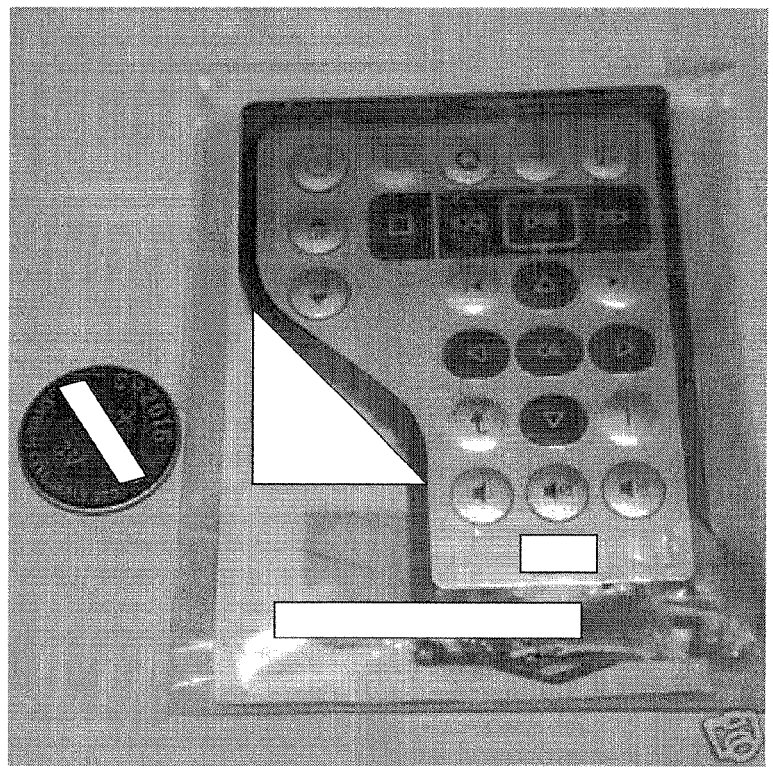
FIG. 4 shows another input device in accordance with an embodiment of the subject invention.

FIG. 3 shows a back view of the input device of FIG. 1 301 along with a wireless receiver device 303 in accordance with an embodiment of the subject invention. Here, a radio frequency (RF) receiver is shown capable of receiving RF signals transmitted from the input device 301. In another embodiment, Infrared (IR) communication is utilized. As discussed above, other communication technologies are known in the art and may be used with the subject invention.

Figure 5:
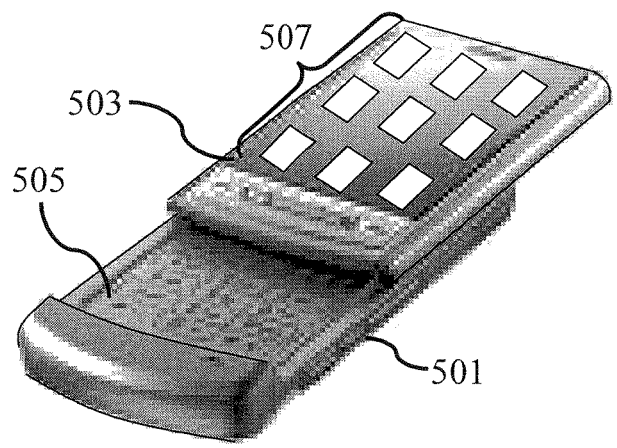
FIG. 5 shows yet another input device in accordance with an embodiment of the subject invention.

FIGS. 4-9 show other input devices that can be used with a system in accordance with an embodiment of the subject invention. FIG. 5 shows an input device 501 which includes a simple push-button interface 503, including a number of buttons 507, and a more complex interface 505, which is revealed when the simple interface 503 slides laterally. In an embodiment of the subject invention, the simple interface 503 may be used by a patient or untrained user to enter data, while the more complex interface 505 is available to another set of users such as, hygienists, nurses, dentists, doctors, or other trained professionals, or habituated users.

In another embodiment, a switch or other control is provided on the input device for activating, deactivating, or changing a set of controls on the input device. For example, the Num Lock key 111 (displayed in FIG. 1) may perform this function, In a further embodiment, back lighting or other lighting is used to change the information displayed on one or more keys. In a simplified mode, unused keys can be "blacked-out" or different colors and/or symbols can be displayed on the same key to indicate different functions. This feature avoids the problem of keys appearing too busy with indications of multiple functions being presented at the same time. In another embodiment, the input device has multiple interfaces presented on different sides of the input device. For example, controls for a patient or novice user are arranged on one side of the input device, and controls for an examiner or trained user are arranged on another side of the input device.

The ability to switch between trained and novice input modes or interfaces enables a trained staff member to enter some of the data and then hand the input device to the patient or more novice user for other data entry tasks. This feature limits the errors made by the patient or other inexperienced user.

The advantage of involving the patient in data collection and input is twofold. It is helpful as the patient acts as a second set of hands while the examiner has both hands busy collecting data or performing a procedure. This option also decreases the need for the examiner to break a sterile working field. But the real value is that it involves the patient as a participant in the diagnosis, or co-diagnosis, effort. As dental or medical exam data is entered, the patient becomes more aware of their body and where favorable or problematic results are found. This awareness can be supplemented with audio or visual feedback. Through a feedback module, the host computer or input device can analyze the collected data and present audio or visual feedback to the patient. For example, a speaker can be provided for playing sounds or audio messages to the patient. Or a display device such as a monitor or video goggles can be provided which graphically presents feedback to the patient. As further discussed below, such feedback can be customized based on the data collected from the patient thus far. By having the computer or input device present feedback, the delivery of feedback can be purposely separated away from the examiner to insure a standard message getting to each patient. The computer can then store a record of what specific feedback or educational materials were presented to the user for the purpose of documenting patient education.

Figure 6:
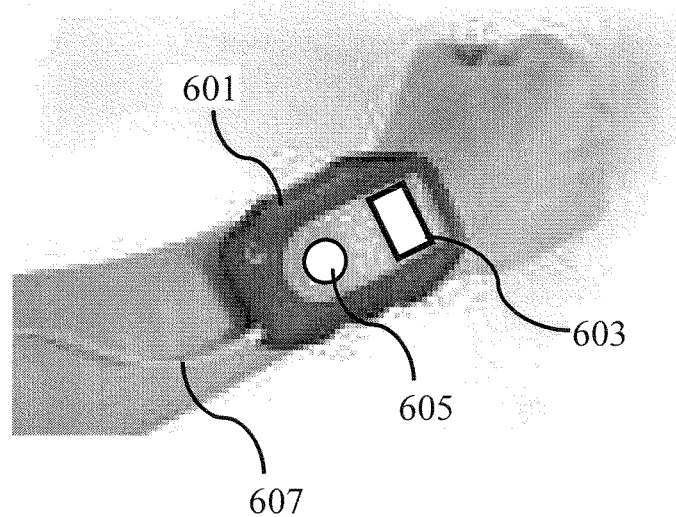
FIG. 6 shows a wearable input device in accordance with an embodiment of the subject invention.

FIG. 6 shows a wearable input device 601 in accordance with an embodiment of the subject invention. This device includes a small key pad 603 for alphanumeric and other custom keyed data entry as described above. The device also includes a trackball 605 which can be used to navigate between fields of a computer-based patient chart as described above or otherwise navigate computer applications as is well known in the art. The device also includes a communication cable 607 for communication to a host computer as discussed above. Input device 601 may be removeably attached to the user via hook and loop fasteners or other adjustable means.

Figure 7:
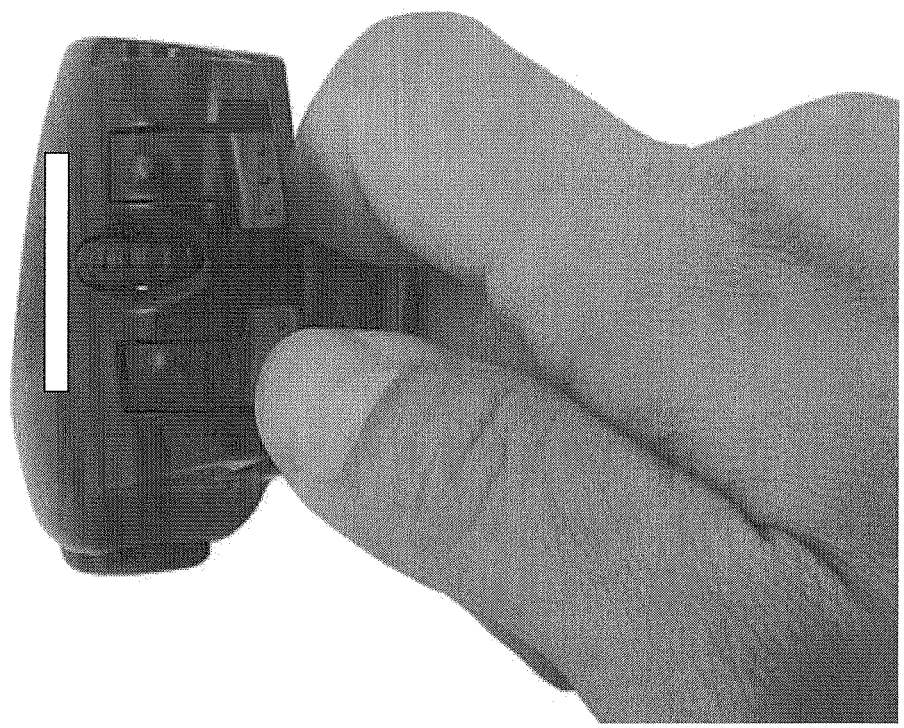
FIG. 7 shows another wearable input device in accordance with an embodiment of the subject invention.

FIG. 7 shows another wearable input device that can be used with an embodiment of the subject invention. The device shown here includes two toggle switches and a scroll wheel, which can be used for data entry or field navigation as described above. The input device can alternatively be worn on a leg, arm, wrist, hand, or finger. In another embodiment, the input device is attached near or on an examination table, chair, or other handy surface. Locking down the position of the input device speeds up data entry as the position is fixed and the user does not have to reorient their hands to the device again and again.

Figure 8:
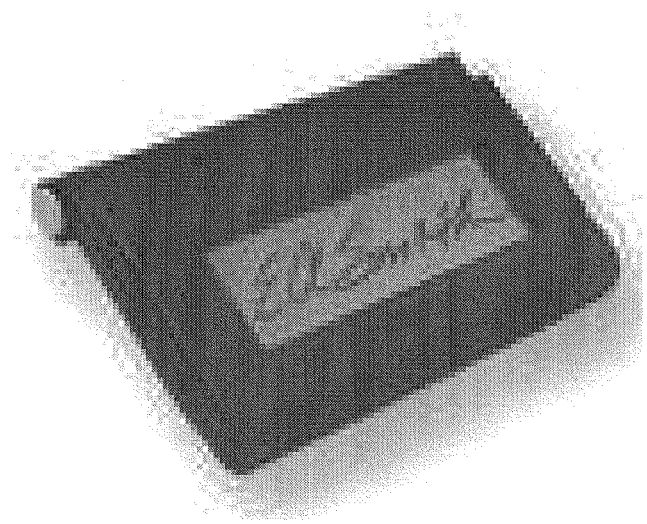
FIG. 8 shows an electronic signature pad in accordance with an embodiment of the subject invention.

FIG. 8 shows an example of an electronic signature pad in accordance with an embodiment of the subject invention. An electronic signature pad, such as the one shown here, can be incorporated into an input device or host computer in accordance with an embodiment of the subject invention. For example, in a particular embodiment, a touch pad on the input device supports dual functions of cursor navigation and a signature pad. In another embodiment, the electronic signature pad can be a standalone device which communicates an electronic signature to a host computer using known communication methods. As further described below, such an electronic signature pad can be used with the subject invention to document consent to or denial of different treatment options presented to the user.

The input device can incorporate or provide USB, or other accessory ports, for the connection of other peripheral devices. For example, a camera can be built into the input device to store pictures or take diagnostic or educational images of or about the patient or related to the patient data. The input device can also contain a bar code reader to scan or display medical information about drugs or prescribed treatments. Possible blood testing or heart monitoring devices can be easily attached to relay additional data to the computer. The input device can also incorporate other diagnostic sensors for detecting, fat levels, mass body index, heart rate, stress levels, or other indicators of health/wellness, while the device is held by the patient. A voice activated microphone can also be incorporated to allow data input via the voice of the examiner or patient. The voice input can be converted to digital signals or keyboard shortcut commands to control the software or other devices.

Figure 9:
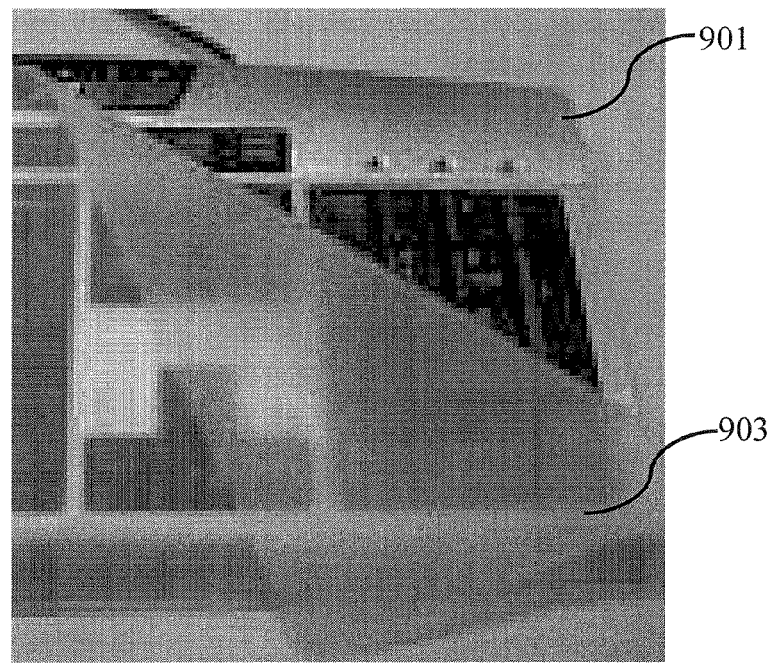
FIG. 9 shows a keyboard input device and an aseptic film in accordance with an embodiment of the subject invention.

FIG. 9 shows a keyboard input device 901 and an aseptic film 903 in accordance with an embodiment of the subject invention. As is well known in the art, maintenance of a sterile working field is important for many medical and dental examinations and procedures. The aseptic film can be used to cover the keys or other input controls of the input device 901. The film or cover can then be cleaned or replaced between patients.

An aseptic film is only one possible device and method for avoiding cross-contamination. Other devices and methods are known in the art and can be used with the subject invention. For example, plastic bags can be custom made to fit various devices. The bags can then either be cleaned, disinfected, or disposed of between patients. A bag or film can completely surround an input device or can have an eclectic edge to attach when clipped in or attached to something else. Or magnetism, static electricity, or other known mechanism, may be used to hold a protective plastic cover/barrier to a portion of an input device. Or the input device can incorporate a roll of film or bags attached on the top or bottom of the input device. A user pulls a new film from the roll as needed. In another embodiment, the keys or other input controls present a flat surface to be easily disinfected and cleaned between each patient use. In an alternate embodiment, the keys are raised, but sealed so that they can be sprayed down without damage to electronics. Other asepsis devices and methods are well known in the art and can be used with the subject invention.

The preceding examples of input devices are merely illustrative. Other input devices are well known in the art and may also be used with the subject invention.

In an embodiment of the subject invention, the input device works in unison with a host computer and a feedback module to automatically present visual, audio and other feedback to the examiner or the patient. Feedback can be immediate or delayed until the end of an examination or procedure or other time period. Feedback can serve numerous purposes including confirming that data was entered correctly and communicating/confirming progress through an ordered chart or other sequenced record. As discussed above, an examiner can pre-set the path or sequence of the examination before the examination begins. As data is entered, sound feedback can then be provided to confirm the progress of the examination along the pre-set path. For example, during a periodontal exam the feedback module can indicate: "you are crossing the midline"; "you are changing arches"; "you are at the lower arch/jaw"; "you are now entering recession mode"; "you are done"; or other signposts. This feature allows an experienced examiner to complete an exam without watching a screen to make sure data points are being entered in the appropriate fields.

In a preferred embodiment of the invention, feedback serves to educate the patient on the nature and progress of an asymptomatic disease. In an embodiment of the invention, feedback is standardized to ensure a consistent message is delivered. In a further embodiment, feedback is customized based on collected patient data. In yet another embodiment, the timing and type of feedback provided are stored as documentation of patient education. Feedback can be supplied through any number of output devices and can take any number of forms. For example, feedback can have audio, visual, tactile, and other components. It can include video, graphics, holographs, sounds, voice, paper reports, emails, and other presentation media known in the art. Various output devices known in the art can be used to produce feedback, including but not limited to monitors, video goggles, and other display devices, speakers, and other audio devices, printers, websites, emails, and other communication and publication technologies. The output can be presented locally and at remote locations.

Figure 10:
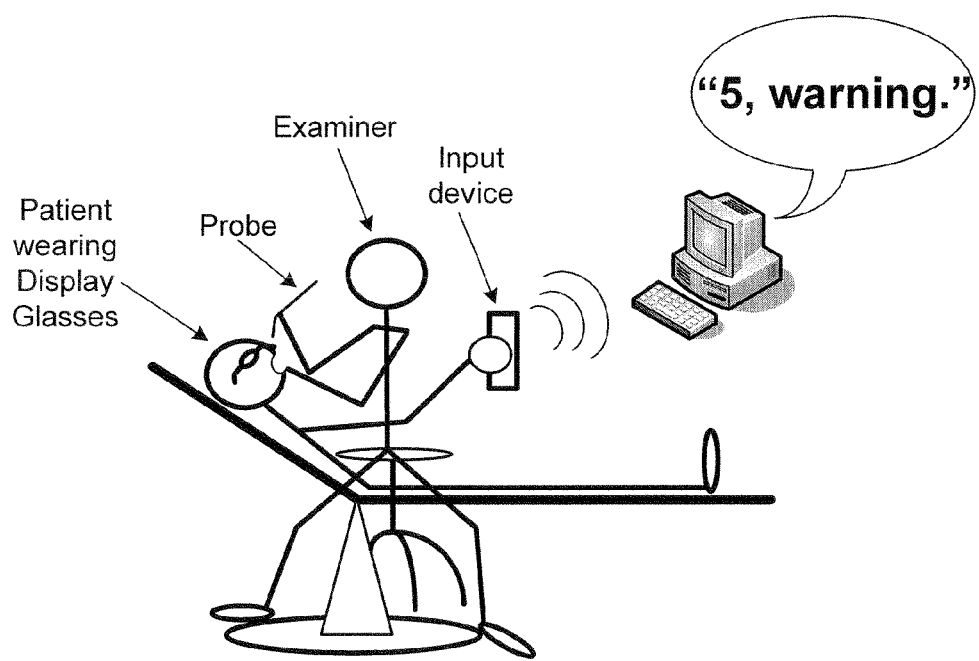
FIG. 10 shows a line drawing of a periodontal examination using a system in accordance with an embodiment of the subject invention.

FIG. 10 shows a line drawing of a periodontal examination using a system in accordance with an embodiment of the subject invention. Here, a patient is being examined by an examiner holding a periodontal probe. The patient holds an input device, and as the examiner calls out data points for the examination, the patient enters the data points into the input device. The input device wirelessly communicates the data points to a host computer which analyzes and stores the data and provides feedback via a feedback module. Here, the examiner measured a periodontal depth of 5; the patient entered this data point by pressing a red five on the input device; and the computer responded via the feedback module, "5, warning," confirming the data entered and providing an indication of the nature and progress of the patient's periodontal disease. In this embodiment of the subject invention, the patient wears video display glasses which protect the patient's eyes during the examination while providing an opportunity for immediate visual feedback as well. For example, as the warning is sounded, the video display glasses could present an appropriate image of a tooth with a periodontal gap of depth 5.

Configuration options can be set at the time of examination (or preset for each user, each patient, each input terminal, or each installation site, among other possibilities) which determine the type of feedback that is presented to the user in a given situation. For example, "healthy," "warning," and "danger" levels can be set. Standard messages can be selected or input by the user. For example, a practitioner may choose to record his or her own standard audio or video messages which can be stored and presented to the user via the feedback module as appropriate.

Presenting feedback via an independent, objective source such as a video or recorded or computerized voice may provide many benefits to patients and practitioners. First, it allows the feedback to be standardized and documented regardless of any reluctance a particular examiner might have about delivering bad news to the patient. Second, the patient may respond differently to such feedback. The patient may view the computer, video, voice, or other presentation as more authoritative, or the patient may feel less embarrassed or emotional when receiving feedback from a non-human actor. This decreased emotional reaction may help the patient instead focus constructively on need treatment.

Figure 11:
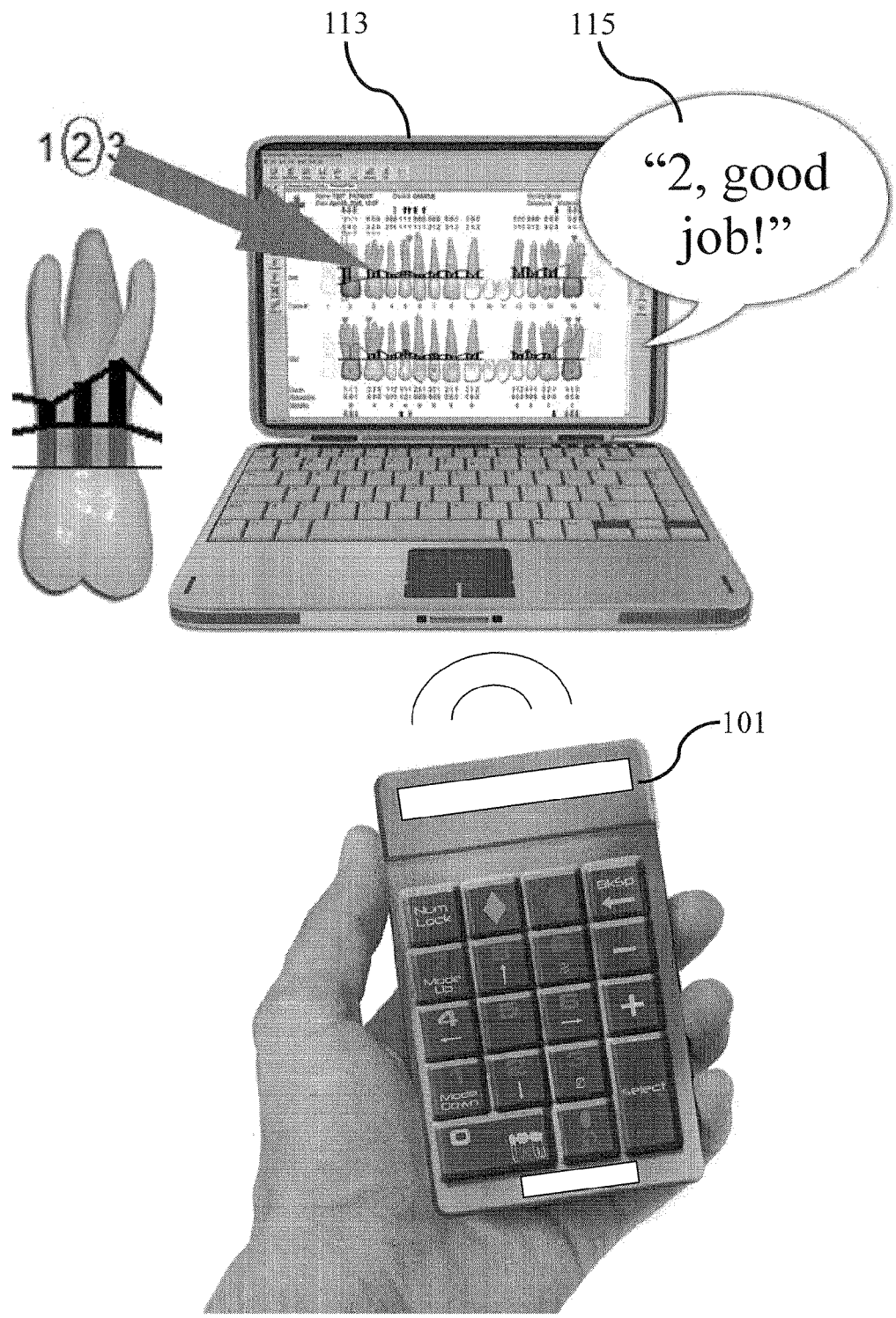
FIG. 11 shows a pictorial representation of a system in accordance with an embodiment of the subject invention.

FIG. 11 shows a pictorial representation of a system in accordance with an embodiment of the subject invention. In this example, an input device 101 communicates wirelessly with a host computer 113 which then produces an audio feedback message 115 and updates a patient information interface to provide visual feedback as well. Here, a two was entered on the input device 101 corresponding to a periodontal measurement of 2. The input device 101 communicates the data point 2 to the host computer 113. The host computer 113 then analyzes and stores the new data point and provides feedback via the feedback module. The periodontal measurement of 2 was an improvement over the measurement taken and stored during the prior examination, so the appropriate feedback "good job" is presented. The appropriate field on the patient information interface is also updated to the new measurement and a trend error is added visually showing the positive trend.

Figure 12:
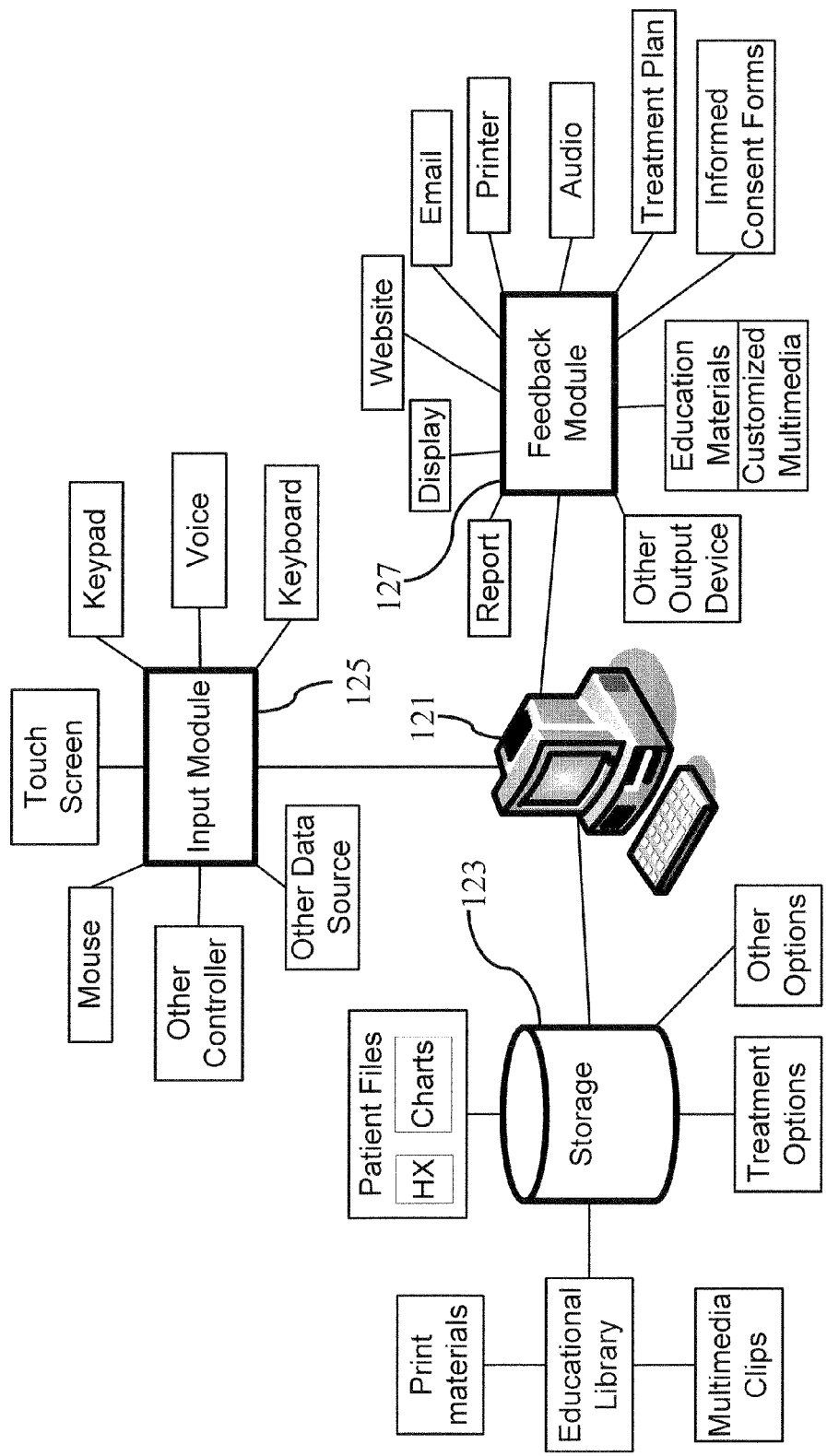
FIG. 12 shows a functional block diagram of a system in accordance with an embodiment of the subject invention.

FIG. 12 shows a functional block diagram of a system in accordance with an embodiment of the subject invention. This system includes a host computer 121, a storage device 123, an input module 125, and a feedback module 127. The functions of all of these elements can be held in a single device or the functions of each can be distributed over multiple devices. Such devices can be local to each other or distributed remotely over a wireless or wireline, local or wide area network. Embodiments of the invention may contain additional elements not presented or may not include all of the elements presented here.

The host computer 121 can comprise any number of computers including laptops, desktops, and server configurations. The host computer 121 is connected to the storage device 123 and can store and retrieve various data to and from the storage device 123. The storage device 123 may comprise any number of various media for storing data. The data stored may include patient files including patient information and charts, an educational library including print materials such as authoritative articles and published facts and multimedia clips such as video, audio, and graphics clips.

Treatment options and other pre-set options may also be stored. Such options can control the course of examination and what types of feedback are provided to the patient. A practitioner may preset such options for each user, each patient, each input terminal, or each installation site, among other possibilities. For example, the practitioner may indicate a treatment plan to be delivered as feedback to a patient when data is collected within given parameters. The system can suggest particular treatment options to the practitioner based on published facts and the practitioner can either accept, modify, or substitute different treatment options, or vary the given parameters as the practitioner's judgment directs.

The input module 125 provides data to the host computer 121 via various input devices and sources. For example, the input can be from any of the input devices discussed above or can come from another controller or data source. For example, patient data may be electronically transferred from another doctor's office, or may be entered through an online form, among other possible sources. The host computer 121 can store all or some of the data collected from the input module in the storage device 123.

The host computer 121 utilizes the feedback module 127 to provide feedback to patients and others in various forms. Some feedback options are depicted here, including the provision of a report, a visual display, publishing information to a website or via email, and other options. As will be obvious to those in the art, other feedback options are also available and may be used with the subject invention. As discussed above, pre-set options can be used to control the format and content of feedback provided via the feedback module 127.

Figure 13:
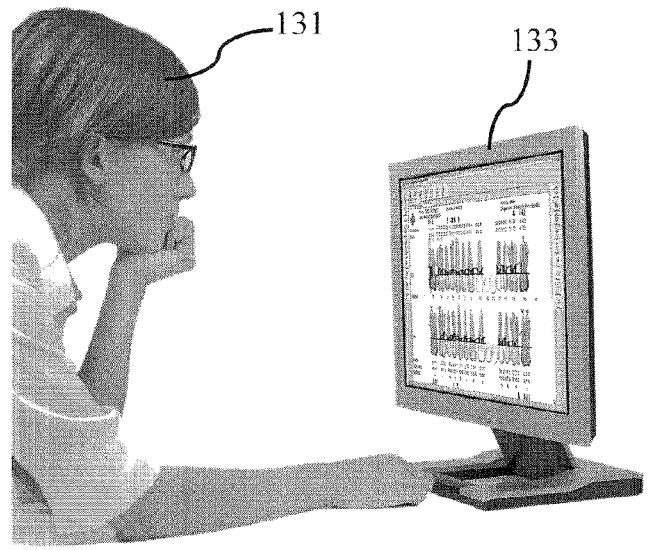
FIG. 13 shows a display device in accordance with an embodiment of the subject invention.

FIG. 13 shows a display device 133 in accordance with an embodiment of the subject invention. The display is viewed by a viewer 131, which may be an examiner, a patient, or other practitioner or staff member involved in the patients treatment.

Figure 14:
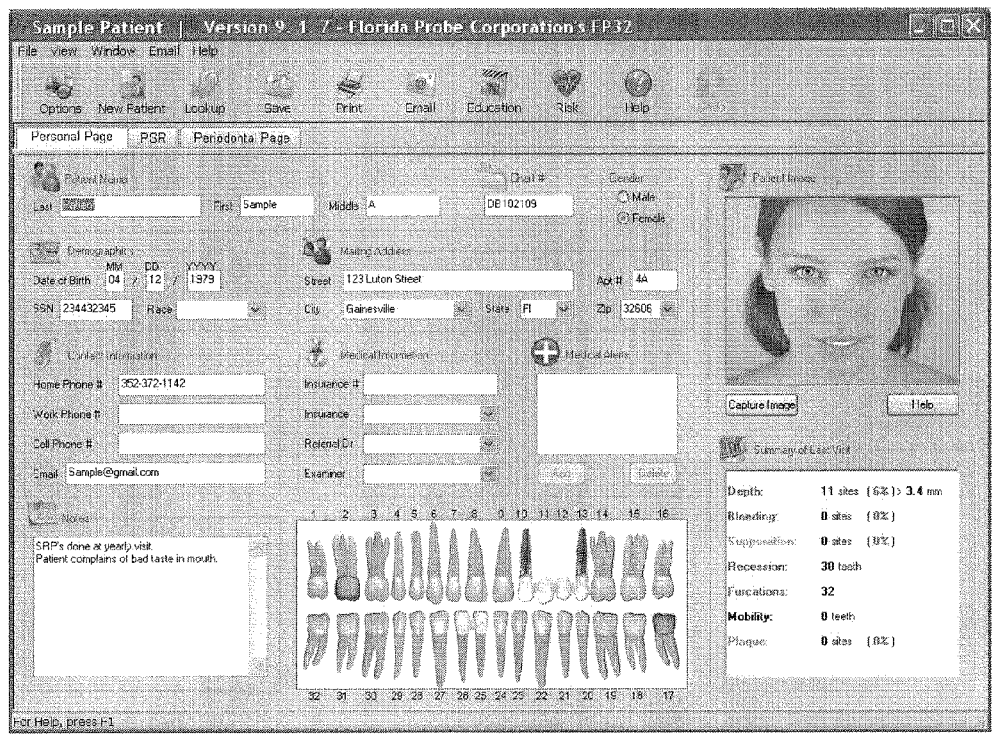
FIG. 14 shows a screen image of a graphical user interface in accordance with an embodiment of the subject invention.

FIG. 14 shows a screen image of a graphical user interface in accordance with an embodiment of the subject invention. The interface presented is only one example of an interface that may be used to collect patient data. Other configurations are possible including more, less, or different data fields and feedback elements. The example presented here relates to dental treatment of a patient, but a similar interface can be adapted relating to medical treatment.

Figure 15:
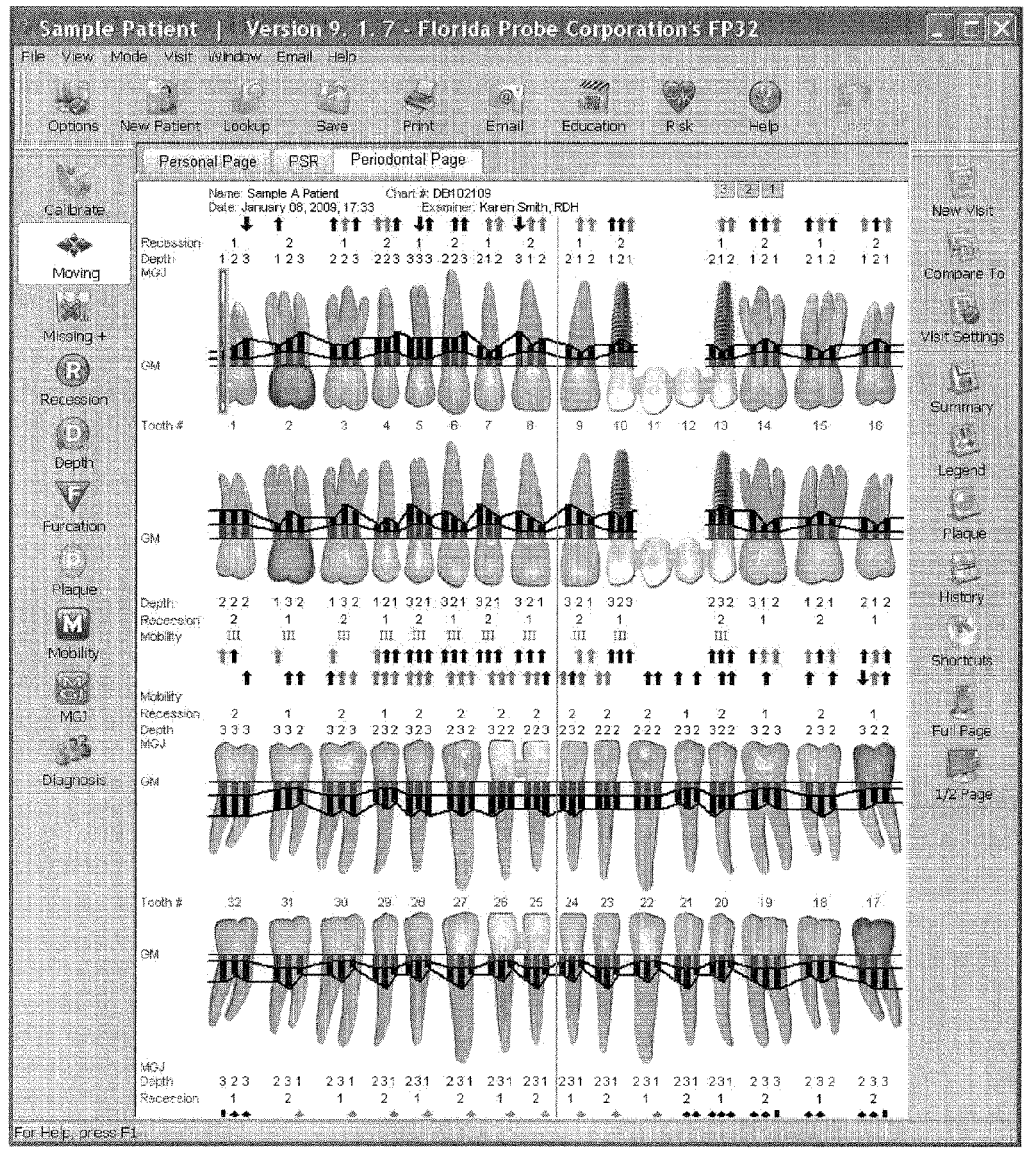
FIG. 15 shows a screen image of a patient information interface in accordance with an embodiment of the subject invention.

FIG. 15 shows a screen image of a patient information interface in accordance with an embodiment of the subject invention. The appearance and style of this interface is a trademark of Florida Probe Corporation. This interface is only one example. Other configurations are possible including more, less, or different data fields and feedback elements. The example presented here relates to periodontal charting, but a similar interface can be adapted for other treatments.

Figure 16:
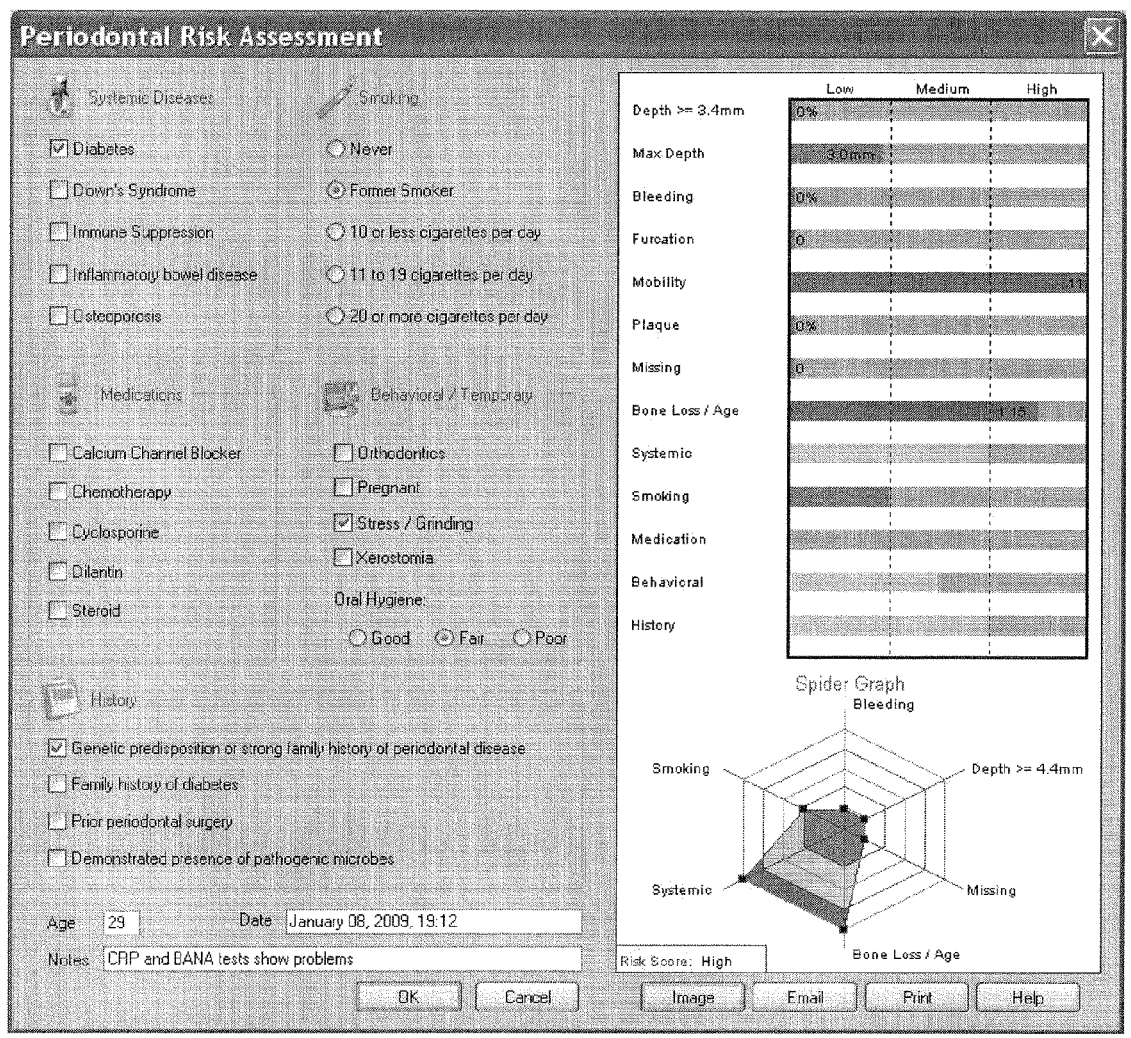
FIG. 16 shows a screen image of a risk assessment interface in accordance with an embodiment of the subject invention.

FIG. 16 shows a screen image of a risk assessment interface in accordance with an embodiment of the subject invention. Again this interface is only one example. Other configurations are possible including more, less, or different data fields and feedback elements. The example presented here relates to periodontal risk assessment, but a similar interface can be adapted for other types of risk assessment.

In an embodiment of the subject invention, data collected via the various interfaces shown in FIGS. 14-16 can be entered via an input module such as input module 125 and stored in a stored a storage device such as storage device 123. The data collected can be analyzed via a host computer such as host computer 121 and appropriate feedback can be presented via a feedback module such as feedback module 127.

Figure 17:
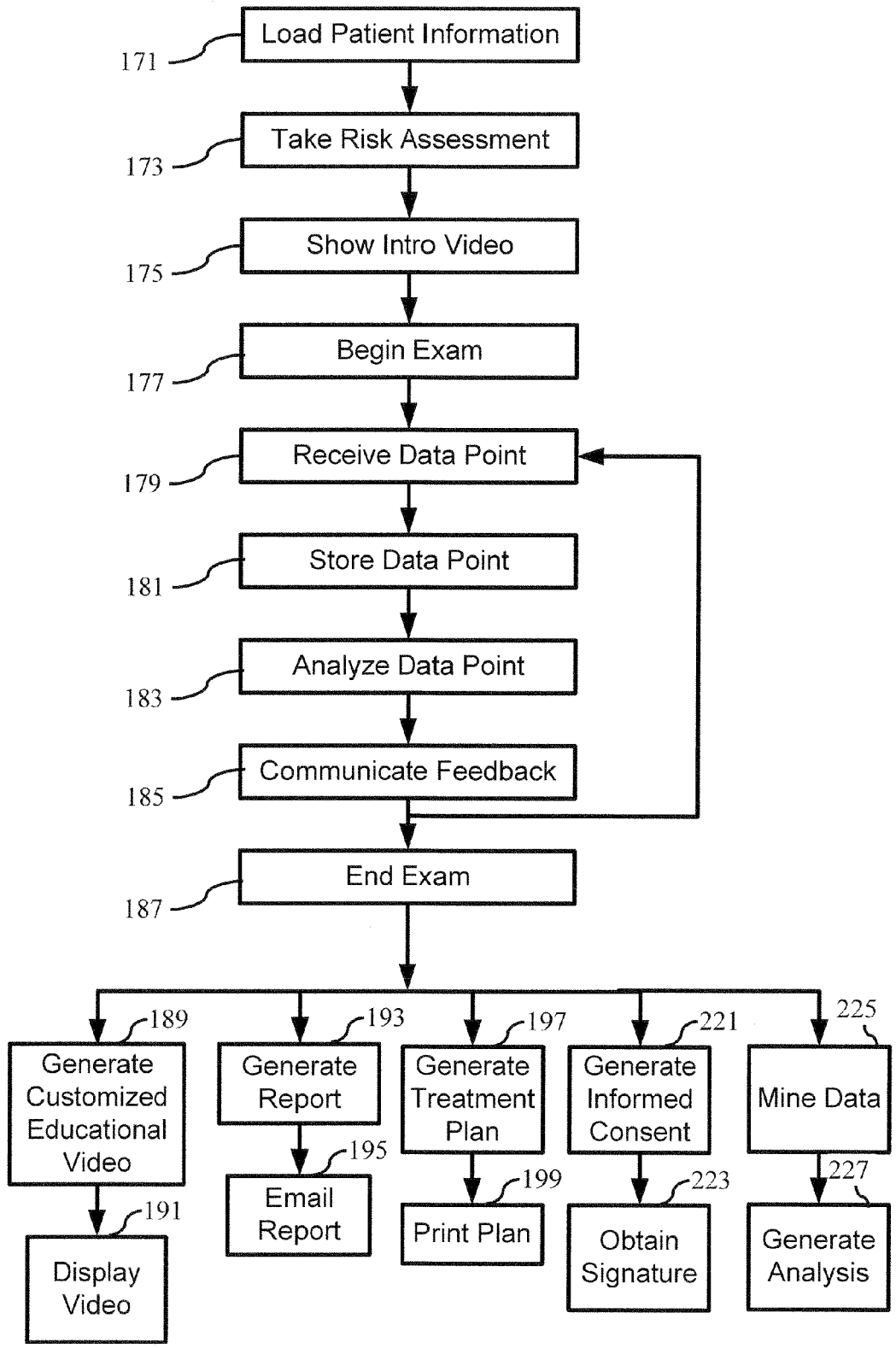
FIG. 17 shows a flow diagram of a method in accordance with an embodiment of the subject invention.

FIG. 17 shows a flow diagram of a method for performing an examination on a patient in accordance with an embodiment of the subject invention. At step 171, information about the patient is loaded into a host computer such as host computer 121. Such information may be retrieved from a storage device such as a storage device 123 and may include patient history, prior charts, and other applicable information. Alternatively, new patient information may have been obtained from the patient prior to the examination. Such information may be collected by means of an input module such as input module 125 or may be collected by one paper and later input into such an input module. In a particular embodiment, the patient emails information to an email address associated with the practitioner prior to the examination. Such email can then be automatically or manually entered into an input module such as input module 125. In yet another embodiment, patient data is retrieved from a third party software system such as a practice management software system.

At step 173, a risk assessment questionnaire is administered to the patient who collects additional patient data relevant to the examination. The questionnaire can be filled out directly through a risk assessment interface such the one shown in FIG. 16 or the questionnaire can be given verbally or in writing and later input into such an input module such as input module 125. The additional data is then stored in a storage device 123 for use in later steps.

At step 175, an introductory video is presented to the patient to educate the patient about the examination to follow. The video can be drawn from educational materials stored on a storage device such as storage device 123, and selected according to preset options also stored on such a device. The presentation of the video is accomplished by means of a feedback module such as feedback module 127. Such presentation can be made via a computer monitor or other display device, such as video goggles. A time stamp and identifying information about the video is recorded in a storage device such as storage device 123 to document the patient's education. The video can include educational materials to begin to educate the patient regarding possible diagnosis and treatments that may be indicated by the examination. In an embodiment, the video contains information specific to a practice where the examination is taking place. In a further embodiment, the video is customized based on information loaded in step 171 or acquired in step 173. For example, the name and age of the patient may be used. Specific risk factors indicated may control what video clips are included in the presentation. For example, a patient who smokes may be shown a video clip that educates the patient of the increased risks of smoking related to the examination.

At step 177, the examination itself begins. As discussed above, the examination may follow a pre-set sequence. At a step 179, a first data point is received via an input module such as input module 125. As shown in FIG. 11, the data point is then passed to a host computer such as host computer 113. At a step 181, the data point is stored via a storage device such as storage device 123.

At step 183, the data point received in step 179 is analyzed to determine appropriate feedback to communicate to the patient. Such analysis may include combining the data with other patient information previously collected in steps 171, 173, and previous iterations of step 181. The analysis may also include comparing the data and the other patient information to established parameters stored as preset options in a storage device such as storage device 123.

At step 185 the appropriate feedback determined by step 183 is presented to the patient. Such feedback may include an audio message such as a positive or negative voice message or a sound such as a siren, warning, or danger sound. A voice message may comprise a short phrase such as "bleeding gums" or a longer description of the patient's condition. Feedback may also include a video or tactile component, such as hepatic response from the input device held by the patient. As described above, in an embodiment of the subject invention, a timestamp and description of the feedback provided is stored via a storage device such as storage device 123.

After step 185, the method continues with either a return to step 179 when another data point is received via an input module such as input module 125, or the examination ends at a step 187. The end of the examination can be indicated via an input module such as input module 125 or the examination may time-out and proceed to step 187.

At step 187, patient information collected during the examination is again analyzed to determine appropriate feedback. This analysis is similar to that performed at step 183. It may take into account any all previous information collected during the examination. It may also select feedback according to pre-set options stored in a storage device such as storage device 123. In a preferred embodiment of the invention a wider range of feedback options is available at this time as shown steps 189-227. Multiple paths may be taken from the step 187 and the paths may proceed in parallel or in series.

For example, the method may proceed to steps 189 and 191, in which a customized educational video is generated and displayed to the patient. The video is customized with patient specific information as discussed in relation to a step 175, but additional patient information is now available and a longer, more tailored and comprehensive video may now be generated. For example, the video may include a diagnosis resulting from the examination as well as in formation on recommended treatment options.

The method may also proceed to steps 193 and 195, in which a report of the examination is generated and emailed to the patient or other interested party, such as a specialist. The report may include information from the examination or other risk assessment information such as that presented in the interfaces shown in FIGS. 15 and 16. Instead of or in addition to being emailed, the report may be visually displayed on a monitor and/or printed and/or published in another known manner, such as via a website.

At steps 197 and 199, a treatment plan is generated and printed for the patient. In various embodiments of the invention, the treatment plan is emailed instead of or in addition to being printed, and/or displayed on a monitor and/or published in another known manner, such as via a website. As discussed above, the treatment plan can be generated based on preset treatment options which have been approved or customized by a practitioner. The treatment plan generated may not be limited to a treatment. Instead it may include a continued series of treatments over a period of time or a lifetime.

At step 221, informed consent forms corresponding to a selected treatment plan (such as a treatment plan generated in step 197) are generated for the patient's review. Such consent forms can be generated based on preset options which have been approved or customized by a practitioner. At a step 223, the patient's signature is obtained accepting treatment. In a preferred embodiment, a signature is also obtained when treatment is declined in order to document the patient's actions. In a further embodiment of the invention, the signature is obtained via an electronic signature pad such as the pad depicted in FIG. 8. The electronic signature is then stored as part of the patient's file in a storage device such as storage device 123.

As discussed above, timestamps and descriptions of the feedback provided may also be stored at this time. Such data and other patient information may be automatically distributed in accordance with a selected treatment such as a treatment plan selected in a step 197. For example, such data and patient information may be emailed to other health care professionals, (such as specialists, insurance companies, and other authorized agents) to continue treatment. The treatment pain may include automated follow up emails via a feedback module such as the feedback module 127 or additional health questionnaires to fill out via an input module such as the input module 125.

At a next patient visit, the examination may repeat with additional information and feedback options. For example, the intro video of step 175 may be further customized. Also, feedback regarding trends can be given similar to that discussed in reference to FIG. 11.

Thus, in embodiments of the invention the method depicted in FIG. 17 or a similar method recurs to create a continuous feedback loop in which additional patient information is obtained via an input module such as input module 125. The additional patient information is then assessed by a host computer such as host computer 121 along with previously obtained patient information stored in a storage device such as storage device 123 to produce customized feedback delivered via a feedback module such as feedback module 127. Part of the feedback given may direct the patient to an input module such as an input module 125. This direction can include but is not limited to directing the patient to return for a follow-up appointment, directing the patient to fill out an online questionnaire, or other input method previously discussed or known in the art. The loop then cycles yet again, thereby engaging the patient in a customized and continuous diagnosis and treatment experience. As discussed above, this feedback loop can cycle when the patient comes in for another office visit, but the loop my also cycle based on email, website, phone, or other out-of-office interaction with the patient.

Finally, at steps 225 and 227, patient information can be mined and an analysis generated. Such mining can include data collected from any and all patients in a particular office, site installation, or practice. Such mining may analyze the financial health of the office or identify patients that missed appointments or otherwise failed to follow-up on their treatment plans. In a further embodiment, the resulting analysis includes recommendations for new or different treatment options based on published facts. In yet another embodiment, practitioners can anonymously post information about problem or great teaching cases automatically through the feedback module. Such post information can include patient treatment history, examination results over many visits, summary data, as well as other pertinent information. The patient name and other identifying information can automatically be stripped from the post information to comply with H.I.P.P.A.

In a further embodiment of the invention, data may also be aggregated and mined by third parties such as providers of system elements and public health organizations such as the National Institute of Health. The resulting analysis may spot new trends or link new diseases.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

Many different arrangements of the various components depicted, as well as components not shown, are possible without departing from the spirit and scope of the present invention. Embodiments of the present invention have been described with the intent to be illustrative rather than restrictive. A skilled artisan may develop alternative means of implementing the aforementioned improvements without departing from the scope of the present invention. It will be understood that certain features and subcombinations are of utility and may be employed without reference to other features and subcombinations and are contemplated within the scope of the claims. Not all steps listed in the various figures need be carried out in the specific order described.

It should also be understood that, although the present invention has been described with reference to specific details of certain embodiments thereof, it is not intended that such details should be regarded as limitations upon the scope of the invention except as and to the extent that they are included in the accompanying claims.

I claim:

1. A method for providing a customized feedback related to a condition of a patient, comprising:
    a) providing one or more input modules for data input, a data storage and processing device, and a feedback module, wherein at least one of the one or more input modules is adaptable between at least two input modes, wherein an interface of a first input mode has a plurality of input controls utilized for data input by a trained user and an interface of a second input mode is utilized for data input by the patient, wherein the second input mode has fewer or simplified input controls compared to the first input mode, and wherein at least one of the one or more input modules is adapted to receive one or more data points via different input modes simultaneously and/or the input module is adapted to switch sequentially for patient input and for trained user input during an examination of the patient and receive one or more data points via the different input modes sequentially during the examination of the patient;
    b) performing on the patient a medical examination or a medical procedure related to the diagnosis and/or treatment of a periodontal disease;
    c) collecting a data point related to the diagnosis and/or treatment of periodontal disease;
    d) inputting the data point into one of the one or more input modules that has been adapted to one of the at least two input modes;
    e) transmitting the data point from the input module to the data storage and processing device and storing the data point in the data storage and processing device, wherein the data point is stored momentarily, temporarily, or permanently;
    f) processing the data point via the data storage and processing device wherein the data storage and processing device generates at least one of an aural, visual, or tactile customized feedback based upon the data point, wherein the customized feedback is a diagnosis, medical educational material, a medical examination result, a medical opinion, and/or a treatment plan; and
    g) transmitting the customized feedback to the feedback module, so as to be conveyed to the patient directly by the feedback module, wherein the data point is collected during the medical examination or the medical procedure and the customized feedback is conveyed to the patient during or after the medical examination or medical procedure.

2. The method, according to claim 1, wherein the condition of the patient is related to a periodontal disease for which the patient is not aware of any symptoms.

3. The method, according to claim 1, wherein the input control for use by a patient is a hand-held keyboard.

4. The method, according to claim 1, wherein the storage and processing device is a computer.

5. The method, according to claim 1, further comprising storing on the data storage and processing device a record of the customized feedback conveyed to the patient.

6. An automated system for providing a customized feedback related to a condition of a patient, comprising:
    a) one or more input modules for data input with an interface having one or more input controls adapted to receive one or more data points directly from the patient while undergoing a medical procedure related to the diagnosis and/or treatment of a periodontal disease, wherein at least one of the one or more input modules is adaptable between at least two input modes, wherein an interface of a first input mode has a plurality of input controls utilized for data input by a trained user and an interface of a second input mode is utilized for data input by the patient, wherein the second input mode has fewer or simplified input controls compared to the first input mode, and wherein at least one of the one or more input modules is adapted to receive one or more data points via different input modes simultaneously and/or the input module is adapted to switch sequentially for patient input and for trained user input during an examination of the patient and receive one or more data points via the different input modes sequentially during the examination of the patient;
    b) a data storage and processing device adapted to receive the one or more data points, and process the one or more data points, and to generate a customized feedback based upon the processing of at least one data point; and
    c) a feedback module adapted to receive the customized feedback from the data storage and processing device, and present customized feedback, by at least one of aurally, visually, or tactilly, directly to the patient, wherein the customized feedback is a diagnosis, medical educational material, a medical examination result, a medical opinion, and/or a treatment plan.

* * * * *

UNITED STATES PATENT AND TRADEMARK OFFICE
CERTIFICATE OF CORRECTION

| | | |
|---|---|---|
| PATENT NO. | : 8,639,526 B2 | Page 1 of 1 |
| APPLICATION NO. | : 12/713831 | |
| DATED | : January 28, 2014 | |
| INVENTOR(S) | : Chris Gibbs | |

It is certified that error appears in the above-identified patent and that said Letters Patent is hereby corrected as shown below:

In the Specification:

Column 13,
Line 43, "as in formation" should read --as information--.

Column 14,
Line 18, "pain may include" should read --plan may include--.

Signed and Sealed this
Tenth Day of June, 2014

Michelle K. Lee
*Deputy Director of the United States Patent and Trademark Office*